United States Patent [19]

Landsiedel et al.

[11] Patent Number: 5,149,365
[45] Date of Patent: Sep. 22, 1992

[54] DIORGANOTIN COMPOUNDS, AND AGENTS WHICH HAVE A BACTERICIDAL AND FUNGICIDAL ACTION AND CONTAIN THESE COMPOUNDS

[75] Inventors: Horst Landsiedel, Unna; Hans Plum, Hamm-Heessen, both of Fed. Rep. of Germany

[73] Assignee: Schering Aktiengesellschaft, Bergkamen, Fed. Rep. of Germany

[21] Appl. No.: 640,406

[22] PCT Filed: Jun. 22, 1989

[86] PCT No.: PCT/EP89/00704

§ 371 Date: Jan. 22, 1991

§ 102(e) Date: Jan. 22, 1991

[87] PCT Pub. No.: WO90/01033

PCT Pub. Date: Feb. 8, 1990

[30] Foreign Application Priority Data

Jul. 21, 1988 [DE] Fed. Rep. of Germany ....... 3824807

[51] Int. Cl.⁵ ................... C09D 5/14; C01G 19/00
[52] U.S. Cl. .................. 106/18.32; 424/405; 424/409; 424/650; 514/493; 514/741; 534/692; 534/713
[58] Field of Search ............. 106/15.05, 18.32; 424/405, 409, 650; 514/493, 741; 534/692, 713

[56] References Cited

U.S. PATENT DOCUMENTS 3,911,134 10/1975 Pommer et al. ............. 424/274
4,158,001 6/1979 Reuther et al. .

FOREIGN PATENT DOCUMENTS 1176804 10/1984 Canada .
0072426 2/1983 European Pat. Off. .
1024743 2/1958 Fed. Rep. of Germany .
2336290 2/1975 Fed. Rep. of Germany .
2341882 3/1975 Fed. Rep. of Germany .
2633452 1/1978 Fed. Rep. of Germany .
1438154 6/1976 United Kingdom .

OTHER PUBLICATIONS

International Tin Research Institute, Publication No. 559, 1979, Bokranz and Plum, "Fortschritte der chem. Forschung", vol. 16, Issue 3/4, p. 377.

*Primary Examiner*—William R. Dixon, Jr.
*Assistant Examiner*—Anthony J. Green
*Attorney, Agent, or Firm*—Scully, Scott, Murphy & Presser

[57] ABSTRACT

The invention concerns new diorgano tin compounds derived from N-cyclohexyl-N'-hydroxy diazenium oxide, as well as bactericides and fungicides which are suitable as disinfectants, as preservatives for wood and other materials, for bactericidal and fungicidal finishing of textiles, plastics, building materials or as biocides for paint systems and which contain these diorganotin compounds as active ingredients.

8 Claims, No Drawings

DIORGANOTIN COMPOUNDS, AND AGENTS WHICH HAVE A BACTERICIDAL AND FUNGICIDAL ACTION AND CONTAIN THESE COMPOUNDS

The invention relates to new diorganotin compounds which are derived from N-cyclohexyl-N'-hydroxydiazenium oxide, and to agents which have a bactericidal and fungicidal action, are suitable as disinfectants, agents for the protection of wood and materials, for the bactericidal and fungicidal finishing of textiles, plastics, building materials or as biocide for paint systems, and contain these diorganotin compounds as active substances.

The powerful activity of triorganotin compounds against microorganisms, for example harmful fungi and bacteria, is known. In the case of the trialkyltin compounds, the optimum action is reached when the total C number of the alkyl groups bonded to the tin atom is 9–12. Shorter or longer alkyl groups reduce the biocidal activity. Compared with trialkyltin compounds, dialkyltin compounds have a very low biocidal action (International Tin Research Institute, Publication No. 559, 1979; Bokranz, Plum; Fortschritte der chemischen Forschung, Vol. 16, Issue 3/4, p. 377).

DE-C-1,024,743 describes another group of biocides, which is mainly employed as a wood preservative. This group comprises metal salts of N-N'-alkylhydroxydiazenium oxides or N-cyclohexyl-N'-hydroxydiazenium oxides (abbreviated to MeHDO). The drawback of these compounds is that high application concentrations are required for protecting the wood, and that the action against wood-discoloring fungi is relatively low.

For these reasons, mixtures of metal salts of N-cyclohexyl-N'-hydroxydiazenium oxide with other biocides were proposed to increase the activity or to widen the spectrum of action (DE-A-2,336,290, DE-A-2,341,882 and EP-B-0,072,426).

It has furthermore been disclosed that the reaction product TBT-HDO, prepared from tri-n-butyltin chloride and the potassium salt of N-cyclohexyl-N'-hydroxydiazenium oxide (K-HDO), have a very good biocidal activity (DE-A-2,633,452).

Surprisingly, it has now been found that reaction products of dialkyltin compounds with N-cyclohexyl-N'-hydroxydiazenium oxide (abbreviated to $R_2Sn$ HDO) have a very good action against bacteria and fungi, in particular also gram-negative bacteria and wood-destroying and wood-discoloring fungi.

The invention relates to reaction products of dialkyltin compounds with N-cyclohexyl-N'-hydroxydiazenium oxide ($R_2Sn$-HDO) of the general formula

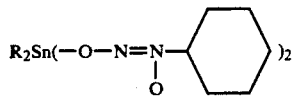

in which R is an alkyl radical having 1 to 12, in particular 3–8, carbon atoms, especially an n-alkyl radical such as n-propyl-, n-butyl-, n-hexyl- or n-octyl, it being possible for the individual radicals R to be identical or different. The di-n-butyltin compound (R=n-butyl; DBT-HDO) is therefore particularly preferred.

The invention furthermore relates to bactericidal and fungicidal agents which contain one or more of the diorganotin compounds $R_2Sn$-HDO according to the invention, for use as agents for wood protection, disinfectants, preservatives for industrial products and for imparting biocidal properties to textiles, plastics or building materials.

The compounds $R_2Sn$-HDO are expediently used in the form of preparations such as solutions, emulsions, dispersions with or without binder, or with solid carriers or diluents and, if appropriate, with the addition of wetting agents, tackifiers, emulsifiers and agents which aid dispersion.

Examples of suitable solvents are alcohols, white spirits, toluene or xylene.

To prepare aqueous formulations, the agents according to the invention can be provided in the form of stable aqueous concentrates which contain customary emulsifiers, preferably nonionic emulsifiers, e.g., alkylaryl polyglycol ethers.

The agents according to the invention can be employed in an outstanding manner in the form of formulations, in particular for the protection of wood, for example for recently felled wood which is readily attacked by bacteria and fungi such as Aspergillus and Trichoderma species; likewise, they are suitable for treating structural timber which is protected against wood-destroying fungi and also against bacterial attack by the biocidal action of the active substances according to the invention.

Furthermore, the agents according to the invention are suitable for imparting biocidal properties to aqueous paint systems, for example dispersions, with regard to shelf life and also for protection against bacterial and fungal attack of the paint, in particular also against the attack of aqueous wood paint systems, for example alkyd resin dispersions, by blueing fungi.

Aqueous formulations can also be used for imparting biocidal properties to a variety of materials such as paper, board, plastics, textiles, glues, building materials and leather.

Another field of application is the equipment of aqueous liquors against undesired microorganisms, for example for cooling circuit water, manufacturing water in paper production, or drilling and cutting oils.

Depending on the field of application, the concentrations of active substance are in the range of from 0.1–5% (wood protection), 0.05–3% (equipping paint systems, papers, textiles, building materials etc.) or 0.0001–0.2% (cooling and manufacturing water, drilling and cutting oils).

To widen the spectrum of action, to obtain a particular action against specific microorganisms or for the equipment with insecticidal properties, the compounds according to the invention may be combined with other active substances. Suitable as such active substances are, inter alia: copper naphthenate, copper-8-oxiquinoline, N,N'-dimethyl-N'-phenyl-N'-fluorodichloromethylthiosulfonyldiamide, N-cyclohexyl-N-methoxy-2,5-dimethylfuran-3-carboxamide, 3-iodo-2-propynylbutyl carbamate, methyl benzimidazole-2-carbamate, N-trichloromethylthiophthalimide, 1-{[2-(2,4-dichlorophenyl)-1,3-dioxolan-2-yl]methyl}-1H-1,2,4-triazole, γ-hexachlorocyclohexane, and synthetic pyrethroids, such as α-cyano-3-phenoxybenzyl 3-(2,2-dichlorovinyl-2,2-dimethyl)cyclopropane-1-carboxylate.

The agents can be applied or incorporated in any desired manner, for example by brushing on, spraying, immersing or by industrial processes such as impregnation under pressure or in vacuo.

The compounds according to the invention are prepared by the following equation.

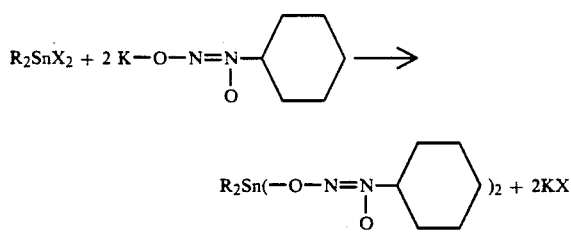

(X=halogen)

According to the invention, diorganotin halides $R_2SnX_2$ are reacted with alkali metal salts of N-cyclohexyl-N'-hydroxydiazenium oxide (Me-HDO) at temperatures of 50° C.-60° C. in aqueous alcoholic solution or organic solvents such as, for example, hexane, during which process the product is obtained in the organic phase. The starting materials can be prepared by known methods (International Tin Research Institute, Publication No. 559, 1979; Bokranz, Plum; Fortschritte der chemischen Forschung, Vol. 16, Issue 3/4, p. 377; DE-A-2,633,452), or are commercially available (SCHERING AG, BASF).

Surprisingly, the diorganotin compounds $R_2Sn$-HDO according to the invention have a wide spectrum of action with a good action against both gram-positive and gramnegative bacteria as well as against wood-destroying and wood-discoloring fungi (Tables 1 and 2). In particular, this is also true for compounds containing alkyl radicals, which contain more than 4 C atoms, for example di-n-octyltin compound. This is surprising insofar as, for example, tri-n-octyltin compounds show no biocidal action as opposed to tri-n-butyltin compounds.

What is remarkable is the fact that the compounds according to the invention are considerably less harmful to the environment compared with triorganotin compounds:

|  | Weight loss 6 days 65° C.) in % | $LD_{50}$ oral (rats) in mg/kg of body wt. | $EC_{50}$ (Orfes*/Daphnia**) in mg/l of water | in mg/l of water |
|---|---|---|---|---|
| TBT-HDO | 12.8 | 63 | 0.035 | 0.020 |
| DBT-HDO | 2.3 | 250-500 | 0.18 | 4.9 |

*Determination in accordance with DIN 38412, Part 15
**Determination in accordance with DIN 38412, Part 12.

As shown by the comparison above, the amount released into the environment during a storage period of 6 days at 65° C. of, for example, TBT-HDO, is nearly six times higher than in the case of DBT-HDO according to the invention.

As demonstrated by the $LD_{50}$ values (oral, rats), the DBT-HDO according to the invention also has a considerably lower toxicity to warm-blooded species than TBD-HDO.

The toxicity to fish and daphnia in the case of the diorganotin compounds $R_2Sn$-HDO according to the invention is in a lower order of magnitude than in the case of the triorganotin compounds $R_3Sn$-HDO.

This proves that the compounds according to the invention are outstanding active substances for biocidal agents with a wide spectrum of action against harmful organisms, while simultaneously being less harmful to the environment.

EXAMPLE 1

Preparation of bis(N-cyclohexyldiazeniumdioxy)di-n-butyltin (DBT-HDO)

To a solution of 151.9 g (0.5 mol) of di-n-butyltin chloride (DBTCl) in 500 ml of methanol there are added in the course of about 20 minutes 182.3 g (1 mol) of the potassium salt of N-cyclohexyl-N'-hydroxydiazenium oxide in the form of a 30% strength aqueous solution. The mixture is subsequently stirred for 1 hour at 50° C.-60° C. During this process, an oily phase separates in the bottom area of the reaction vessel and is subsequently separated off and taken up in 500 ml of heptane. After the mixture has been dried with anhydrous sodium sulfate and filtered, the solvent is distilled off in vacuo. The residue which remains is a solid, slightly colored, pulverulent product of the formula

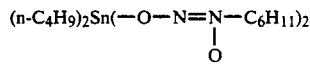

Yield: 222 g (85.5% of theory)
Analysis for $C_{20}H_{40}N_4O_4Sn$ (MW: 519.26):
calculated:
C:46.26%;   H:7.77%;   N:10.79%;   O:12.32%;
Sn:22.86%
found:
C:46.12%;   H:7.71%;   N:10.88%;   O:12.40%;
Sn:22.90%

EXAMPLE 2

Preparation of bis(N-cyclohexyldiazeniumdioxy)di-n-pentyltin (DPT-HDO)

The preparation was effected in analogy to Example 1 using 0.5 mole of di-n-pentyltin dichloride and 1 mole of N-cyclohexyl-N'-hydroxydiazenium oxide.

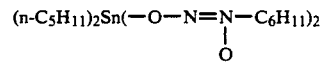

DPT-HDO is an oily, yellow liquid.
Yield: 237 g (86.6% of theory)
Analysis for $C_{22}H_{44}N_4O_4Sn$ (MW 547.31):
calculated:
C:48.28%;   H:8.10%;   N:10.24%;   O:11.69%;
Sn:21.69%
found:
C:48.43%;   H:8.03%;   N:10.11%;   O:10.60%;
Sn:21.83%

EXAMPLE 3

Preparation of bis(N-cyclohexyldiazeniumdioxy)di-n-octyltin (DOT-HDO)

The preparation is effected analogously to Example 1 using 0.5 mole of di-n-octyltin dichloride and 1 mole of N-cyclohexyl-N'-hydroxydiazenium oxide.

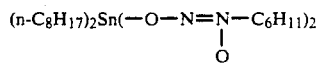

DOT-HDO is an oily, yellow liquid.
Yield: 261.7 g (82.9% of theory)
Analysis for $C_{28}H_{56}N_4O_4Sn$ (MW: 631.47):
calculated:
C:53.26%; H:8.94%; N:8.87%; O:10.13%; Sn:18.80%
found:
C:52.35%; H:8.82%; N:8.96%; O:10.24%; Sn:18.63%

BACTERICIDAL ACTION

The bactericidal test of the compound DBT-HDO according to the invention (cf. Example 1) was effected as an agar diffusion test (cf. Table 1). DST agar was inoculated with 1 drop of a Müller-Hinton broth of the test organisms, diluted 1 : 10. After a prediffusion period of 2 hours at 22° C., the paper filters which had been soaked with solutions of active substance of various concentrations were placed on the agar. The inhibition zones (distance of the cloudy area from the edge of the paper filter in mm) were determined after an incubation time of 24 hours.

FUNGICIDAL ACTION

The inhibition action against fungi, of the products according to the invention, was tested using the "filter disk test" (cf. Table 2). For this purpose, paper filter disks ($\phi$ 5.5 cm) were soaked in ethanolic solutions containing various amounts of active substance. After the filters had dried under room conditions, they were placed on Petri dishes containing plate-count agar which had been inoculated with a spore suspension. The nutrient medium used was biomalt agar 8° Bg, and the dishes were incubated for 3 weeks at +30° C. Thereafter, the sizes of the inhibition zones (distance of the fungal growth from the edge of the filter, in mm) around the samples were determined.

To compare the fungicidal action against Basidiomycetes, small blocks made of pine sapwood (5 cm×2.5 cm×1.5 cm, direction of fiber: 5 cm) were soaked with solutions of graduated concentrations of the active substance DBT-HDO (cf. Example 1) in acetone, based on DIN 52 176.

For comparison reasons, the starting materials di-n-butyltin dichloride and the K salt of N-cyclohexyl-N'-hydroxydiazenium oxide were included in the investigations.

The soaked blocks were kept for 4 weeks in an environmentally-controlled chamber at an air temperature of 20° C. and a relative atmospheric humidity of 65%. They were then subjected to a leaching procedure in accordance with DIN EN 84. After drying, the treated small blocks together with in each case one untreated comparison block were incorporated in Kolle dishes on a pure-breed culture of Coniophora puteana and in this way exposed to attack by the fungus for 16 weeks at 22° C. and 70% relative atmospheric humidity. The effect of the fungi on the individual blocks was determined by calculating the weight losses (based on the dry weights). The limits which were determined in this way and which are expressed by two figures, the lower of which being the highest amount of protective agent (in kg/m³ of wood) at which an attack still took place (weight loss>3%), and the higher denoting the lowest amount from which an attack no longer took place, are listed in Table 3.

TABLE 3

| Limits against Coniophora puteana after leaching treatment kg of product per m³ of wood | |
| --- | --- |
| Di-n-butyltin dichloride | 2.8–4.4 |
| K-HDO | 1.8–3.4 |
| DBT-HDO | 0.51–0.88 |

TABLE 1

Result of the examination for bactericidal properties in the agar diffusion test (inhibition zone in mm)

| Current No. | Active sub. | Active substance conc. of the soaking solution in % | Gram-positive | | Gram-negative | |
| --- | --- | --- | --- | --- | --- | --- |
| | | | Bacillus subtilis | Staphilococcus aureaus | Proteus vulgaris | Escherichia coli |
| 1 | TBT Cl | 0.5 | 19 | 25 | 5 | 0 |
| 2 | TBT-HDO | 0.5 | 18 | 24 | 7 | 0 |
| 3 | DBT-HDO | 0.5 | 15 | 10 | 12 | 3 |
| 4 | K-HDO | 0.5 | 9 | 19 | 0 | 0 |
| 5 | TBT Cl | 0.3 | 18 | 25 | 5 | 0 |
| 6 | TBT-HDO | 0.3 | 22 | 32 | 7 | 0 |
| 7 | DBT-HDO | 0.3 | 11 | 10 | 13 | 2 |
| 8 | K-HDO | 0.3 | 4 | 14 | 0 | 0 |
| 9 | TBT Cl | 0.1 | 19 | 31 | 5 | 0 |
| 10 | TBT-HDO | 0.1 | 17 | 28 | 6 | 0 |
| 11 | DBT-HDO | 0.1 | 6 | 8 | 12 | 0 |
| 12 | K-HDO | 0.1 | 4 | 8 | 0 | 0 |
| 13 | 0 sample | — | 0 | 0 | 0 | 0 |

Figure of merit 0: no inhibition action

TABLE 2

Filter disk test against fungi (determination of the inhibition zones (IZ) around the samples in mm (+ = sample slightly covered in growth, ++ = medium degree of growth, +++ = sample completely covered in growth)

| Active substance | Content of the solution in % | Cladosporum herbarum | | Lentinus lepideus | | Poria monticola | | Paecilomyces varioti | |
| --- | --- | --- | --- | --- | --- | --- | --- | --- | --- |
| | | IZ | Growth | IZ | Growth | IZ | Growth | IZ | Growth |
| Potassium salt | 2 | 10–12 | — | >15 | — | 10–12 | — | 8–10 | — |

TABLE 2-continued

Filter disk test against fungi (determination of the inhibition zones (IZ) around the samples in mm (+ = sample slightly covered in growth, ++ = medium degree of growth, +++ = sample completely covered in growth)

| Active substance | Content of the solution in % | Cladosporum herbarum IZ | Growth | Lentinus lepideus IZ | Growth | Poria monticola IZ | Growth | Paecilomyces varioti IZ | Growth |
|---|---|---|---|---|---|---|---|---|---|
| of N-hydroxy- | 1 | 8–10 | — | 10–12 | — | 6–8 | — | 6–8 | — |
| N-cyclohexyl-diazenium oxide | 0.5 | 4–6 | — | 4–6 | — | 2–3 | — | 5–7 | — |
| Di-n-butyltin | 2 | 0 | ++ | 0 | + | 0 | + | 0 | ++ |
| dichloride | 1 | 0 | ++ | 0 | ++ | 0 | + | 0 | ++ |
|  | 0.5 | 0 | +++ | 0 | +++ | 0 | +++ | 0 | +++ |
| Di-n-octyltin | 2 | 0 | +++ | 0 | ++ | 0 | + | 0 | +++ |
| dichloride | 1 | 0 | +++ | 0 | +++ | 0 | ++ | 0 | +++ |
|  | 0.5 | 0 | +++ | 0 | +++ | 0 | +++ | 0 | +++ |
| Product of | 2 | 8–10 | — | >15 | — | 12–15 | — | 10–12 | — |
| Example 1 | 1 | 5–6 | — | >15 | — | 12–12 | — | 8–10 | — |
| DBT-HDO | 0.5 | 3–5 | — | >15 | — | 6–8 | — | 6–8 | — |
| Product of | 2 | 6–8 | — | >15 | — | 10–12 | — | 10–12 | — |
| Example 2 | 1 | 5–7 | — | >15 | — | 8–10 | — | 8–10 | — |
| DPT-HDO | 0.5 | 2–3 | — | >15 | — | 6–8 | — | 6–8 | — |
| Product of | 2 | >15 | — | >15 | — | 8–10 | — | 10–12 | — |
| Example 3 | 1 | 12–15 | — | >15 | — | 8–10 | — | 8–10 | — |
| DOT-HDO | 0.5 | 10–12 | — | >15 | — | 5–6 | — | 5–6 | — |
| TBT-HDO | 2 | >15 | — | >15 | — | 15 | — | >15 | — |
|  | 1 | >15 | — | >15 | — | 15 | — | >15 | — |
|  | 0.5 | 10–12 | — | >15 | — | 7–9 | — | 10–12 | — |
| 0 sample | — | 0 | +++ | 0 | +++ | 0 | +++ | 0 | +++ |

FORMULATION EXAMPLE 1

A wood undercoat which is colorless and contains little binder and consists of

| | |
|---|---|
| 2.5 | parts by weight of reaction product of Example 1, |
| 0.2 | part by weight of permethrin (cis: trans ratio 25:75), |
| 5 | parts by weight of diethylene glycol monobutyl ether, |
| 6 | parts by weight of alkyd resin having long term oily properties. and |
| 86.3 | parts by weight of white spirit. | shows good penetrability and can be applied to the wood surface in amounts of 100–200 g/m², for example by immersion or brushing on.

FORMULATION EXAMPLE 2

A colored varnish for wood protection, consisting of

| | |
|---|---|
| 3 | parts by weight of reaction product of Example 3, |
| 25 | parts by weight of alkyl resin having long term oily properties [sic] (33% phthalate resin, about 67% triglycerides of vegetable fats), |
| 0.5 | part of weight of desiccants (Co, Mn, Pb salts), |
| 7.8 | parts by weight of red iron oxide paste, |
| 0.7 | part by weight of black iron oxide paste, |
| 5 | parts by weight of diethylene glycol monobutyl ether and |
| 58 | parts by weight of white spirit, | is suitable for painting wooden structural elements with dimensional accuracy, such as, for example, window frames, doors etc. . .

FORMULATION EXAMPLE 3

An active substance solution for the biocidal finishing of textiles, for example cotton canvas, consisting of

| | |
|---|---|
| 3.0 | parts by weight of reaction product of Example 1, |
| 3.4 | parts by weight of micronized polyethylene wax and |
| 95.6 | parts by weight of low-odor, synthetic isoparaffin, | can be applied by spraying the solution or by immersing or soaking the materials to be treated.

FORMULATION EXAMPLE 4

A formulation which can be diluted with water, consisting of

| | |
|---|---|
| 30 | parts by weight of reaction product of Example 2, |
| 48 | parts by weight of non-ionogenic emulsifier, (mixture of polyglycol carboxylates) and |
| 22 | parts by weight of water, | mixed in the sequence indicated, with stirring, gives a preparation which can be diluted with water and which can be employed in concentrations of 1–3% by weight, for example for imparting fungicidal properties to dispersions.

We claim:

1. The reaction product of a dialkyltin compound with N-cyclohexyl-N'-hydroxydiazenium oxide, said reaction product having the general formula

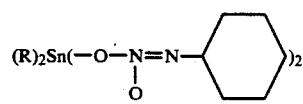

wherein each R, which may be the same or different, is an alkyl radical having 1 to 12 carbon atoms.

2. The reaction product according to claim 1, characterized in that R is an n-alkyl radical having 3 to 8 carbon atoms.

3. The reaction product according to claim 1, characterized in that R is n-butyl.

4. A bactericidal and fungicidal composition comprising a bactericidally and fungicidally effective amount of the reaction product of any one of claims 1 to 3 as the active substance in association with a liquid or solid carrier.

5. A wood protecting composition comprising a wood protecting effective amount of the reaction product of any one of claims 1 to 3 as the active substance in association with a liquid or solid carrier.

6. A process of providing bactericidal and fungicidal properties to textiles, plastics or building materials which comprises applying the composition of claim 4 to a textile, a plastic or a building material.

7. A process for protecting wood which comprises applying the wood protecting composition of claim 5 to wood.

8. A process for imparting biocidal properties to paint which comprises combining a biocidally effective amount of the reaction product of claim 1 with paint.

* * * * *